US008824763B2

(12) United States Patent
Jeon et al.

(10) Patent No.: US 8,824,763 B2
(45) Date of Patent: Sep. 2, 2014

(54) IMAGE RECONFIGURATION METHOD FOR ELECTRO-MAGNETIC TOMOGRAPHY

(75) Inventors: Soon-Ik Jeon, Daejeon (KR); Seong-Ho Son, Daejeon (KR); Hyuk-Je Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 40 days.

(21) Appl. No.: 13/333,280

(22) Filed: Dec. 21, 2011

(65) Prior Publication Data

US 2012/0163690 A1 Jun. 28, 2012

(30) Foreign Application Priority Data

Dec. 22, 2010 (KR) ........................ 10-2010-0132439

(51) Int. Cl.
*G06K 9/00* (2006.01)
*A61B 5/05* (2006.01)

(52) U.S. Cl.
CPC ............. *A61B 5/0507* (2013.01); *A61B 5/0522* (2013.01)
USPC ......................................... 382/131; 382/128

(58) Field of Classification Search
USPC ......................................... 382/128, 131, 132
See application file for complete search history.

(56) References Cited

U.S. PATENT DOCUMENTS

| 2004/0077943 A1* | 4/2004 | Meaney et al. ............... 600/430 |
| 2006/0000982 A1* | 1/2006 | Keller et al. ............. 250/390.08 |
| 2006/0241410 A1 | 10/2006 | Fang et al. |
| 2011/0130656 A1* | 6/2011 | Son et al. ...................... 600/430 |

OTHER PUBLICATIONS

Tonny Rubæk et al., "Nonlinear Microwave Imaging for Breast-Cancer Screening Using Gauss-Newton's Method and the CGLS Inversion Algorithm", IEEE Transactions on Antennas and Propagation, vol. 55, No. 8, Aug. 2007, pp. 2320-2331.

\* cited by examiner

*Primary Examiner* — Tom Y Lu
(74) *Attorney, Agent, or Firm* — Rabin & Berdo, P.C.

(57) ABSTRACT

Disclosed is an image reconfiguration method for electro-magnetic tomography. The image reconfiguration method for electro-magnetic tomography includes: measuring electric field values of each electro-magnetic wave for normal tissue, benign tumor tissue, and cancer tissue that are body tissue properties to perform signal processing on the electric field values of the electro-magnetic waves; calculating the electric field values of the electro-magnetic waves that are subjected to the signal processing as specific image reconfiguration data values; and comparing with the calculated specific image reconfiguration data value and applying to a nonlinear image transform function to convert into amplified image output data value, thereby outputting an image based on the image output data value, wherein the nonlinear image transform function is an exponential function or log function based nonlinear image transform function that selectively amplifies only a difference in the specific image reconfiguration data values between the body tissues.

3 Claims, 5 Drawing Sheets

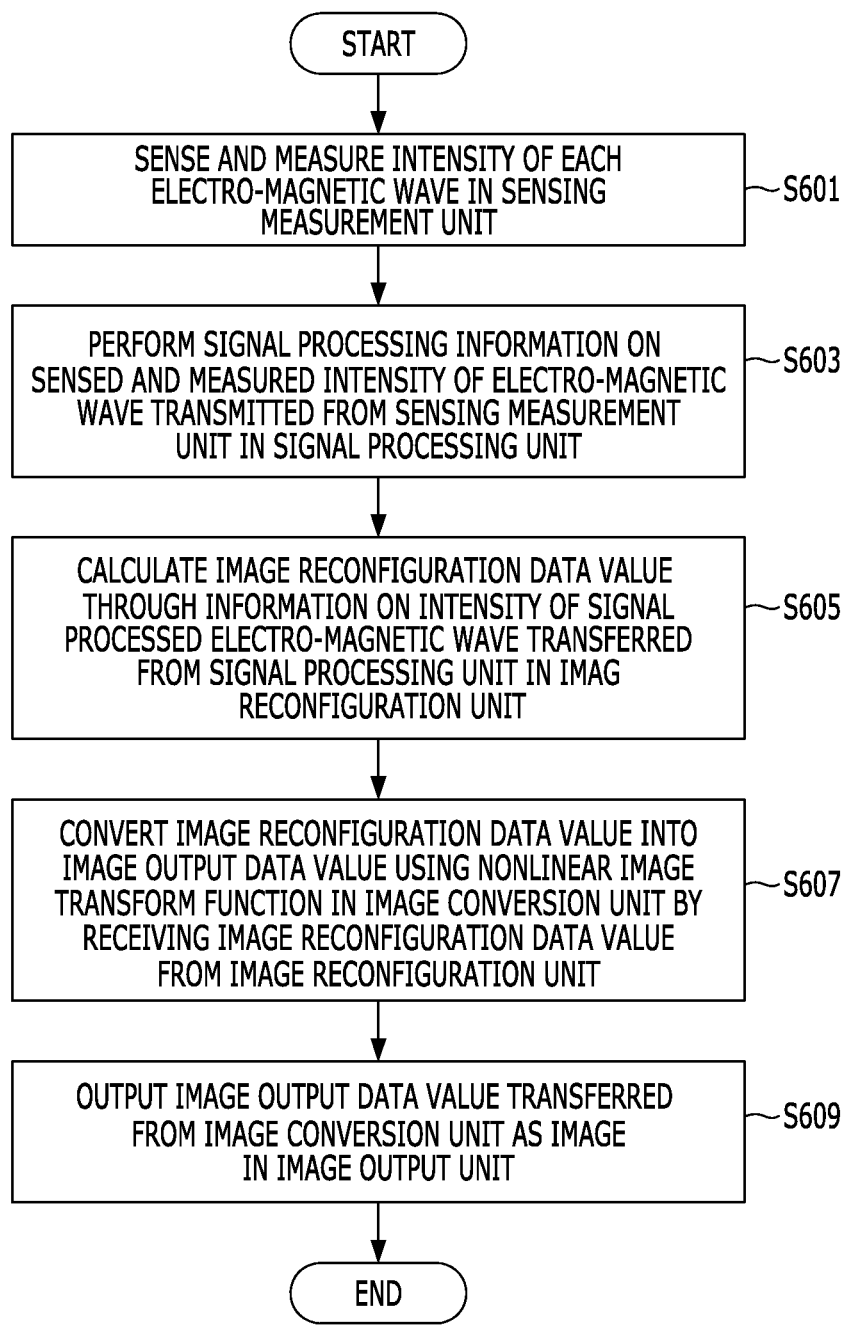

IMAGE RECONFIGURATION METHOD FOR ELECTRO-MAGNETIC TOMOGRAPHY

CROSS-REFERENCES TO RELATED APPLICATIONS

The present application claims priority of Korean Patent Application Nos. 10-2010-0132439 and 10-2011-0116615, filed on Dec. 22, 2010 and Nov. 9, 2011, respectively, which are incorporated herein by reference in their entireties.

BACKGROUND OF THE INVENTION

1. Field of the Invention

Exemplary embodiments relate to an image reconfiguration method for electro-magnetic tomography, and more particularly, to an image reconfiguration method for electro-magnetic tomography diagnosing a cancer that is a method for applying image reconfiguration data values depending on tissue properties in the electro-magnetic tomography to a nonlinear image transform function so as to calculate amplified image output data values, thereby outputting the image.

2. Description of Related Art

An early cancer diagnosis method that has been most frequently used detects a heterogeneous tissue through a mechanical test. Even though a mechanical test method has a relatively simple test process, a diagnosis success rate is extremely low. Therefore, the mechanical test method is performed together with a secondary diagnosis method such as a biopsy. As a result, a need exists for a method for diagnosing a cancer through a more accurately mechanical test.

As a technology for diagnosing a cancer, a technology for linearly outputting an image using propagation characteristics of a radio frequency (RF) electro-magnetic signal having a frequency of 500 MHz to 3000 MHz that is an example of an electro-magnetic wave and enabling a user to the output image has been proposed.

In detail, the general image output method for the electro-magnetic topography in accordance with the related art performs signal processing by sensing and measuring the electro-magnetic wave and generates specific image reconfiguration data values, which are data values for outputting image output data values, through the image reconfiguration. Further, the general image output method linearly outputs the image without changing based on the generated specific image reconfiguration data values and enables a user to recognize the output image.

As described above, the cancer diagnosis method using a linear method through the electro-magnetic wave has a characteristic value ratio relationship in which characteristic values among a normal tissue, a benign tumor tissue, and a cancer tissue approach one another and thus, has the low mutual discrimination and the reduced discrimination intuition, thereby degrading cancer diagnosis accuracy.

SUMMARY OF THE INVENTION

An embodiment of the present invention is directed to a method for applying an image reconfiguration method for electro-magnetic tomography diagnosing a cancer that is a method for applying image reconfiguration data values depending on tissue properties in the electro-magnetic tomography to a nonlinear image transform function so as to calculate amplified image output data values, thereby outputting the image.

The objects of the present invention are not limited to the above-mentioned objects and therefore, other objects and advantages of the present invention that are not mentioned may be understood by the following description and will be more obviously understood by exemplary embodiments of the present invention. In addition, it can be easily appreciated that objects and advantages of the present invention may be implemented by means and a combination thereof described in claims.

An embodiment of the present invention, an image reconfiguration method for electro-magnetic tomography includes: measuring electric field values of each electro-magnetic wave for normal tissue, benign tumor tissue, and cancer tissue that are body tissue properties to perform signal processing on the electric field values of the electro-magnetic waves; calculating the electric field values of the electro-magnetic waves that are subjected to the signal processing as specific image reconfiguration data values; and comparing with the calculated specific image reconfiguration data value and applying to a nonlinear image transform function to convert into amplified image output data value, thereby outputting an image based on the image output data value, wherein the nonlinear image transform function is an exponential function or log function based nonlinear image transform function that selectively amplifies only a difference in the specific image reconfiguration data values between the body tissues.

BRIEF DESCRIPTION OF THE DRAWINGS

FIG. 6 is a flow chart of the image reconfiguration method for electro-magnetic tomography in accordance with the embodiment of the present invention.

DESCRIPTION OF SPECIFIC EMBODIMENTS

Figure 1A:
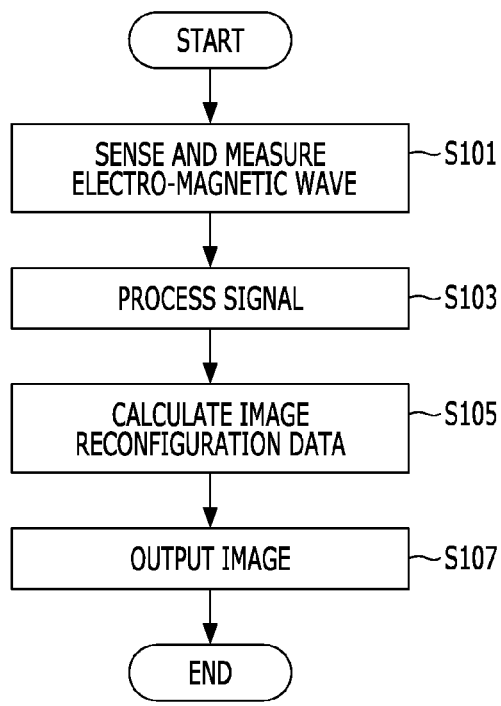
FIGS. 1A and 1B are diagrams for describing a method for linearly outputting an image for general electro-magnetic tomography.

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

Exemplary embodiments of the present invention proposes a method for applying image reconfiguration data values configured depending on tissue properties at a photographing frequency in the electro-magnetic tomography diagnosing a cancer to an exponential function or log function based nonlinear image transform function to calculate image output data values and outputting the image by the calculated image output data values.

Prior to describing the present invention, an electro-magnetic topography method output using a generally linear image output method will be schematically described with reference to FIG. 1.

Figure 1B:
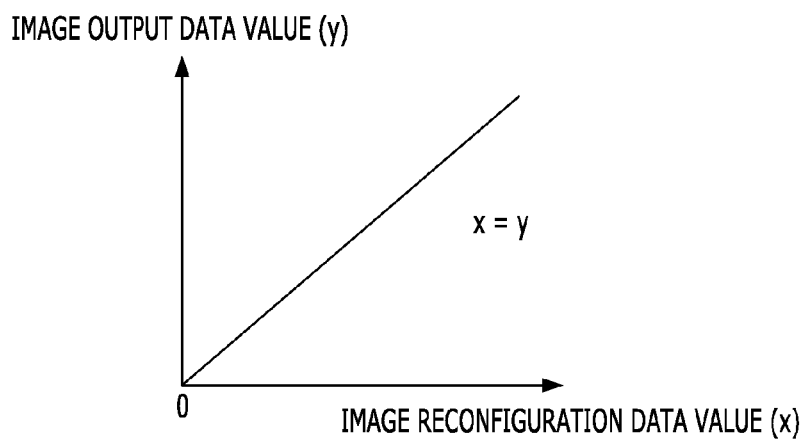

FIGS. 1A and 1B are diagrams for describing a method for linearly outputting an image for general electro-magnetic tomography.

As illustrated in FIG. 1A, a method for linearly outputting an image in electro-magnetic tomography includes sensing and measuring an electro-magnetic wave passing through a specific body tissue in the electro-magnetic tomography (S101) and performs signal processing on the measured electro-magnetic wave (S103). Further, the method calculates specific image reconfiguration data values in order to output the signal processed electro-magnetic wave as an image (S105).

The method calculates the image output data values through the calculated specific image reconfiguration data values to output the image (S107). In this case, the image output data values have a linear relationship which is directly proportional depending on the specific image reconfiguration data values.

In this case, describing with reference to FIG. 1B, FIG. 1B is a graph illustrating a linear relationship (y=x) between the specific image reconfiguration data values and the image output data values. In this case, the specific image reconfiguration data value is referred to as 'X' and the image output data value is referred to as 'y'.

As illustrated in FIG. 1B, it can be confirmed that the image output data values are proportional to the specific image reconfiguration data values depending on the linear relationship.

However, the specific image reconfiguration data values are calculated depending on a system, environment, a length of data and the image output data values may be changed depending on the calculated specific image reconfiguration data values.

Figure 2:
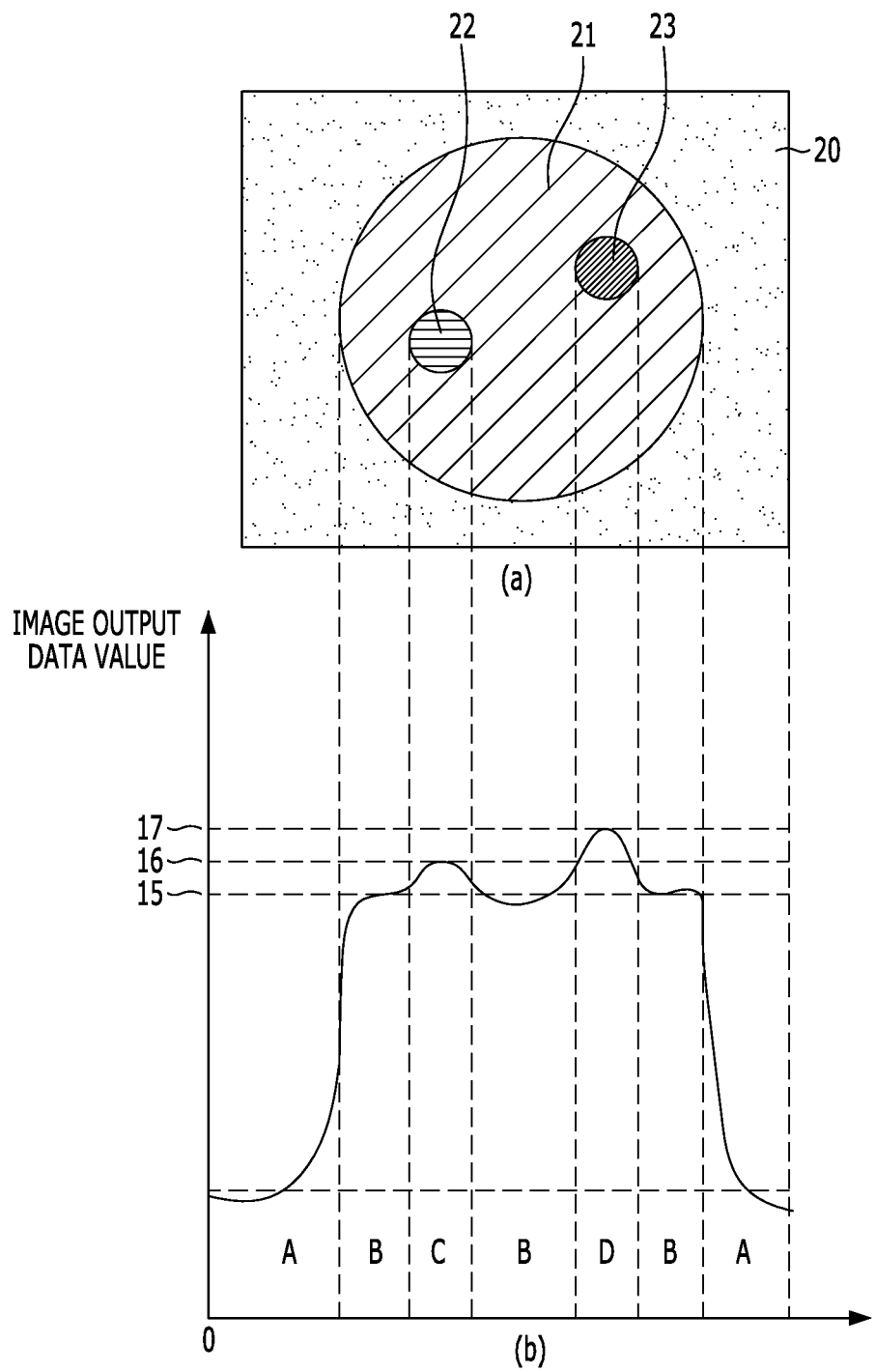
FIG. 2 is an explanation diagram for a photographing image and histogram in accordance with the method for linearly outputting an image for a general electro-magnetic tomography.

FIG. 2 is an explanation diagram for (a) a tomography image and (b) a tomography image histogram in accordance with the method for linearly outputting an image in the general electro-magnetic tomography.

As illustrated in FIG. 2, the tomography image (a) illustrates a background material 20, a normal tissue material 21, a benign tumor tissue 22, and a cancer tissue 23 and the tomography image histogram (b) illustrates the image output data values depending on the tomography image (a).

The tomography image histogram (b) illustrates the image output data values for the background material 20, the normal tissue material 21, the benign tumor tissue 22, and the cancer tissue 23 depending on a body position coordinate (d).

That is, in the tomography image histogram (b), periods 'A' represent the image output data value for the background material 20, periods 'B' represent the image output data value for the normal tissue material 21, periods 'C' represent the image output data value for the benign tumor tissue 22, and periods 'D' represent the image output data value for the cancer tissue 23.

Meanwhile, referring to FIG. 2, the image output data values of some normal tissue materials 21, the benign tumor tissue 22, and the cancer tissue 23 compare with the image output data values of the background material 20 in the body tissue.

For example, in case of a dielectric constant, referring to a ratio relationship of 'normal tissue 21:benign tumor tissue 22:cancer tissue 23:background material 20=50:55:60:20', it can be confirmed that they have a similar ratio relationship. Further, the image output data values calculated through the image reconfiguration do not necessarily coincide with each other.

In the body position coordinate (d) in the tomography image histogram (b), a characteristic value 15 of the normal tissue material, a benign tumor tissue property value 16 in the body position coordinate (d), and a cancer tissue property value 17 in a body position coordinate (d) have the low discrimination and the discrimination intuition, thereby causing the discrimination errors. Therefore, there has been proposed a method for applying the image reconfiguration data values depending on the tissue properties at the photographing frequency in the electro-magnetic tomography diagnosing a cancer to the exponential function or log function based specific nonlinear image transform function to output the image by the amplified image output data values, thereby increasing the discrimination.

Accordingly, the method for increasing discrimination by outputting an image in accordance with the embodiment of the present invention will be described in detail with reference to FIG. 3.

Figure 3:
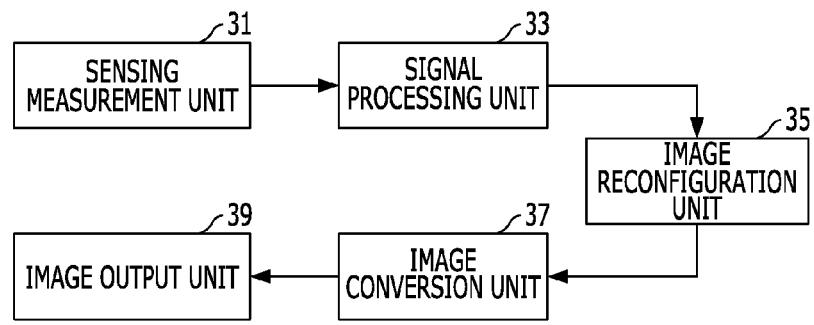
FIG. 3 is a block diagram of an image reconfiguration method for electro-magnetic tomography in accordance with an embodiment of the present invention.

FIG. 3 is a block diagram of the image reconfiguration method for electro-magnetic tomography in accordance with the embodiment of the present invention.

The electro-magnetic tomography system includes a sensing measurement unit 31, a signal processing unit 33, an image reconfiguration unit 35, an image conversion unit 37, and an image output unit 39.

Prior to describing FIG. 3, in the embodiment of the present invention, the image reconfiguration cross section region is a region in which a signal is transmitted and received through a transmitting antenna and a receiving antenna.

The sensing measurement unit 31 measures the intensity of an electro-magnetic wave that is a signal received through at least one receiving antenna receiving a transmitting signal, that is, electric field values of the electro-magnetic waves and transfers the measured electric field values to the signal processing unit 33.

The signal processing unit 33 receiving the electric field values of the electro-magnetic waves from the sensing measurement unit 31 performs the signal processing on the electric field values of the electro-magnetic waves so as to calculate the specific image reconfiguration data values and transfers the signal processed electric field values to the image reconfiguration unit 35.

The image reconfiguration unit 35 calculates the specific image reconfiguration data values and transfers the calculated specific image reconfiguration data values to the image conversion unit 37 so as to reconfigure and output the image.

That is, the image reconfiguration unit 35 performs reverse calculation whether the electric field of each electro-magnetic wave detected through the sensing measurement in the sensing measurement unit 31 is accurately calculated so as to calculate the specific image reconfiguration data values.

In this case, the calculated image reconfiguration data values mean any electrical characteristic distribution values for unknown materials positioned within the image reconfiguration cross section space.

The image conversion unit 37 converts the specific image reconfiguration data values transferred from the image reconfiguration unit 35 into the specific image reconfiguration data values using the non-linear image transform function and transfers the converted specific image reconfiguration data values to the image output unit so as to selectively amplify the frequencies of the image output data values of the normal tissue 21, the benign tumor tissue 22, and the cancer tissue 23 when outputting the image.

As the nonlinear transform function for converting the specific image reconfiguration data values into the image output data values, there is the exponential function or the log function.

First, in order to convert the specific image reconfiguration data values, the image reconfiguration data values of the cancer tissue 23 compares with the image reconfiguration data values of the normal tissue 21 and the benign tumor tissue 22.

In this case, when the image reconfiguration data value of the cancer tissue 23 is higher than the image reconfiguration data value of the normal tissue 21 and the benign tumor tissue 22, the image reconfiguration data value of the cancer tissue 23 is applied to the exponential function based nonlinear image transform function, wherein the exponential function may be represented by the following Equation 1.

$$y = e^x - 1 \qquad \text{[Equation 1]}$$

Here, when the specific image reconfiguration data value x is '0', the image output data value is calculated as '0' and when the specific image reconfiguration data value x is '1', the image output data value is calculated as '(e−1)', wherein the calculated value has a value '(e−1)' times larger than 1. Further, when the specific image reconfiguration data value x is '2', the image output data value is calculated as '($e^2$−1)', wherein the calculated value has a value '($e^2$−1)' times larger than 1. When the specific image reconfiguration data value x is '10', the image output data value is calculated as ($e^{10}$−1), wherein the calculated value has a value '($e^{10}$−1)' times larger than 1.

Meanwhile, when the image reconfiguration data value of the cancer tissue 23 is lower than the image reconfiguration data value of the normal tissue 21 and the benign tumor tissue 22, the image reconfiguration data value of the cancer tissue 23 is applied to the log function based nonlinear image transform function, wherein the log function may be represented by the following Equation 2.

$$Y = \log^{(x+1)} \qquad \text{[Equation 2]}$$

Here, when the specific image reconfiguration data value x is '0', the image output data value is calculated as 'log' and when the specific image reconfiguration data value x is '1', the image output data value is calculated as '$\log^2$', wherein the calculated value has a value '$\log^2$' times larger than 1. Further, when the specific image reconfiguration data value x is '2', the image output data value is calculated as '$\log^3$', wherein the calculated value has a value '$\log^3$' times larger than 1. When the specific image reconfiguration data value x is '10', the image output data value is calculated as '$\log^{11}$', wherein the calculated value is '$\log^{11}$' times larger than 1.

As described above, when using the exponential function or log function based nonlinear transform function, the image output data value y is increased while having the nonlinear relation as the specific image reconfiguration data value x is increased and the image conversion unit 37 transfers the calculated image output data value to the image output unit 39.

The image output unit 39 receives the image output data values converting the specific image reconfiguration data values from the image conversion unit 37 by using the exponential function or the log function and outputs the converted image output data values as the image.

Figure 4:
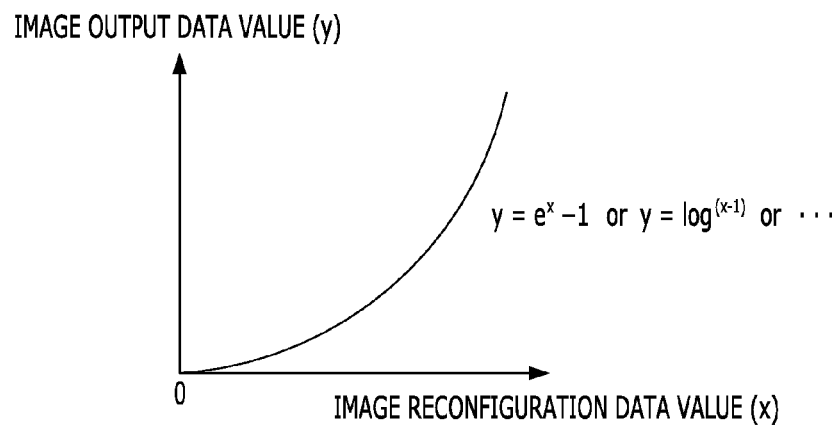
FIG. 4 is a graph for illustrating image output data values using a transform function in the electro-magnetic tomography in accordance with the embodiment of the present invention.

FIG. 4 is a graph for illustrating an image output data values using a transform function in the electro-magnetic tomography in accordance with the embodiment of the present invention.

Referring to FIG. 4, the image output data values amplified and calculated by applying the specific image reconfiguration data values to the exponential function or the log function that is the non-linear transform function are illustrated by a graph and the image output data values are nonlinearly increased according to the increase in the specific image reconfiguration data values.

As described above, when the exemplary embodiment of the present invention uses the exponential function or log function based nonlinear transform function, since the image output data values are increased while having the nonlinear relationship as the specific image reconfiguration data values are increased, the image output data values are calculated as a relatively large value, the discrimination is increased between the small image output data value and the large image output data value, and the visual reading is more definitive as the image output data values are large, compared with the case when the image output data values are small.

Figure 5:
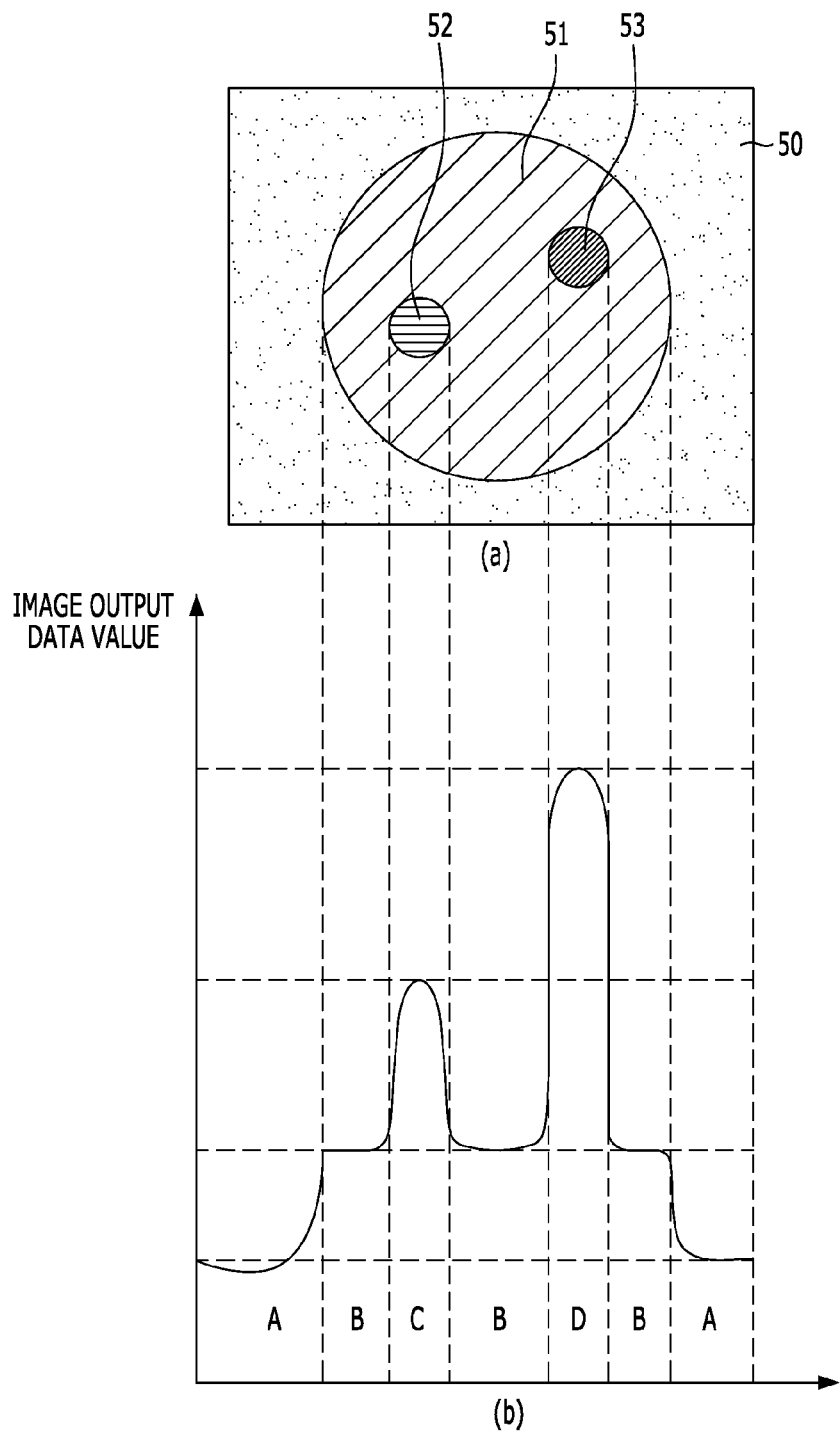
FIGS. 5A and 5B are a tomography image and histogram for the image output method using the transform function in the electro-magnetic tomography in accordance with the embodiment of the present invention.

FIG. 5 is a tomography image (a) and a tomography image histogram (b) for the image output method using the transform function in the electro-magnetic tomography in accordance with the embodiment of the present invention.

The tomography image (a) illustrates the background material 20, the normal tissue material 21, the benign tumor tissue 22, and the cancer tissue 23 and the tomography image histogram (b) illustrates the image output data values of the tomography image (a).

The tomography image histogram (b) is a graph illustrating the image output data values for the background material 20, the normal tissue material 21, the benign tumor tissue 22, and the cancer tissue 23 shown in the tomography image (a) as the image output data values along an X axis, that is, the body position coordinate (d).

That is, in the tomography image histogram, periods 'A' represent an image output data value for the background material 20, periods 'B' represent the image output data value for the normal tissue material 21, periods 'C' represent the image output data value for the benign tumor tissue 22, and periods 'D' represent the image output data value for the cancer tissue 23.

In addition, describing the image output data value for the period 'B' (normal tissue material 21), the image output data value for the period 'C' (benign tumor tissue 22), and the image output data value for the period 'D' (cancer tissue 23), it can be confirmed that the difference in the values between the tissues is clearly shown.

FIG. 6 is a flow chart of the image reconfiguration method for electro-magnetic tomography in accordance with the embodiment of the present invention.

Referring to FIG. 6, the sensing measurement unit 31 measures the intensity of the electro-magnetic wave that is the signal received through at least one receiving antenna receiving the transmitting signal, that is, the electric field values of the electro-magnetic waves and transfers the measured electric field values to the signal processing unit 33 (S601).

The signal processing unit 33 receiving the electric field values of the electro-magnetic waves from the sensing measurement unit 31 performs the signal processing on the electric field values of the electro-magnetic waves so as to calculate the specific image reconfiguration data values and transfers the signal processed electric field values to the image reconfiguration unit 35 (S603).

The image reconfiguration unit 35 calculates the specific image reconfiguration data values and transfers the calculated specific image reconfiguration data values to the image conversion unit 37 so as to reconfigure and output the image (S605).

That is, the image reconfiguration unit 35 performs reverse calculation whether the electric field of each electro-magnetic wave detected through the sensing measurement in the sensing measurement unit 31 is accurately calculated so as to calculate the specific image reconfiguration data values.

In this case, the calculated image reconfiguration data values mean any electrical characteristic distribution values for unknown materials positioned within the image reconfiguration cross section space.

The image conversion unit 37 converts the specific image reconfiguration data values transferred from the image reconfiguration unit 35 into the image output data values using the non-linear image transform function and transfers the converted specific image reconfiguration data values to the image output unit 39 so as to selectively amplify the frequency of the image output data values of the normal tissue 21, the benign tumor tissue 22, and the cancer tissue 23 when outputting the image (S607).

As the nonlinear transform function for converting the specific image reconfiguration data values into the image output data values, there is the exponential function or the log function.

First, in order to convert the specific image reconfiguration data values, the image reconfiguration data values of the cancer tissue 23 compare with the image reconfiguration data values of the normal tissue 21 and the benign tumor tissue 22 and when the image reconfiguration data value of the cancer tissue 23 has a higher value than the image reconfiguration data values of the normal tissue and the benign tumor tissue 22, the image reconfiguration data values are applied to the exponential function $y=e^x-1$.

Here, when the specific image reconfiguration data value x is '0', the image output data value is calculated as '0' and when the specific image reconfiguration data value x is '1', the image output data value is calculated as '(e−1)', wherein the calculated value has a value '(e−1)' times larger than 1. Further, when the specific image reconfiguration data value x is '2', the image output data value is calculated as '($e^2$−1)', wherein the calculated value has a value '($e^2$−1)' times larger than 1. When the specific image reconfiguration data value x is '10', the image output data value is calculated as ($e^{10}$−1), wherein the calculated value has a value '($e^{10}$−1)' times greater than 1.

Second, when the image reconfiguration data value of the cancer tissue 23 has a lower value than the image reconfiguration data value of the normal tissue 21 and the benign tumor tissue 22, the image reconfiguration data value is applied to $y=\log^{(x+1)}$ that is the log function.

Here, when the specific image reconfiguration data value x is '0', the image output data value is calculated as 'log' and when the specific image reconfiguration data value x is '1', the image output data value is calculated as '$\log^2$', wherein the calculated value has a value '$\log^2$' times larger than 1. Further, when the specific image reconfiguration data value x is '2', the image output data value is calculated as '$\log^3$', wherein the calculated value has a value '$\log^3$' times greater than 1. When the specific image reconfiguration data value x is '10', the image output data value is calculated as '$\log^{11}$', wherein the calculated value is '$\log^{11}$', times greater than 1.

As described above, when using the exponential function or log function based nonlinear transform function, the image output data value y is increased while having the nonlinear relation as the specific image reconfiguration data value x is increased and the image conversion unit 37 transfers the calculated image output data values to the image output unit 39.

The image output unit 39 receives the image output data values converting the specific image reconfiguration data values from the image conversion unit 37 by using the exponential function or the log function and outputs the converted image output data values as the image (S609).

As set forth above, the image reconfiguration method for electro-magnetic tomography in accordance with the exemplary embodiments of the present invention can selectively amplify only the difference in the specific values among the normal tissue, the benign tumor tissue, and the cancer tissue having the low discrimination by applying the image reconfiguration data values depending on the tissue properties in the photographing frequency to the exponential function or log function based nonlinear image transform function. Further, the image reconfiguration method for electro-magnetic tomography can make the difference in the values among the normal tissue, the benign tumor tissue, and the cancer tissue clear to increase the doctor's intuition for discrimination at the time of diagnosis, thereby reducing the misdiagnosis rate.

While the present invention has been described with respect to the specific embodiments, it will be apparent to those skilled in the art that various changes and modifications may be made without departing from the spirit and scope of the invention as defined in the following claims.

What is claimed is:

1. An image reconfiguration method for electro-magnetic tomography, comprising:
    measuring intensity of an electro-magnetic wave, and performing signal processing on the measured intensity of the electro-magnetic wave;
    calculating a first image reconfiguration data value using the processed measured intensity of the electro-magnetic wave; and
    converting the first image reconfiguration data value into an image output data value, including
        comparing the first image reconfiguration data value with a second image reconfiguration data value corresponding to an electro-magnetic wave passing through normal tissues and benign tumor tissues,
        when the first image reconfiguration data value is higher than the second image reconfiguration data value, amplifying a difference between the first and second image reconfiguration data values using an exponential function-based nonlinear image transform function, and
        when the first image reconfiguration data value is lower than the second image reconfiguration data value, amplifying the difference between the first and second image reconfiguration data values using a log function-based nonlinear image transform function.

2. The image reconfiguration method of claim 1, wherein when the first image reconfiguration data value is higher than the second image reconfiguration data value, the image output data value is calculated using $$y=e^x-1$$

where x represents the first image reconfiguration data value and y represents the image output data value.

3. The image reconfiguration method of claim 1, wherein when the first image reconfiguration data value is lower than the second image reconfiguration data value, the image output data value is calculated using $$y=\log^{(x+1)}$$

where x represents the first image reconfiguration data value and y represents the image output data value.

* * * * *